United States Patent [19]

Takács et al.

[11] Patent Number: 4,861,888
[45] Date of Patent: Aug. 29, 1989

[54] PROCESS FOR THE PREPARATION OF 3,4-DIHYDROISOQUINOLINE

[75] Inventors: Kálmán Takács; Ilona K. Ajzert, both of Budapest; Katalin M. Kellner, Biatorbágy; Judit Fleischer; Mariann E. Puskás, both of Budapest; József Rimai, Budaors, all of Hungary

[73] Assignee: Chinoin Gyogyszer es Vegyeszeti Termekek Gyara Rt., Budapest, Hungary

[21] Appl. No.: 196,221
[22] PCT Filed: Jul. 17, 1987
[86] PCT No.: PCT/HU87/00030
§ 371 Date: May 11, 1988
§ 102(e) Date: May 11, 1988
[87] PCT Pub. No.: WO88/00586
PCT Pub. Date: Jan. 28, 1988

[30] Foreign Application Priority Data

Aug. 17, 1986 [HU] Hungary .............. 2958/86

[51] Int. Cl.$^4$ .......................................... C07D 217/02
[52] U.S. Cl. .................................................. 546/150
[58] Field of Search ....................................... 546/150

[56] References Cited

U.S. PATENT DOCUMENTS

| 3,135,759 | 6/1964 | Whittaker ............... 546/150 |
| 3,796,715 | 3/1974 | Weimgruber et al. ..... 546/150 |
| 4,656,279 | 4/1987 | Okazaki et al. ......... 546/150 |

Primary Examiner—Glennon H. Hollrah
Assistant Examiner—James H. Turnipseed
Attorney, Agent, or Firm—Herbert Dubno

[57] ABSTRACT

The invention relates to a process for the preparation of 3,4-dihydroisoquinoline by dehydrogenation of the 1,2,3,4-tetrahydroisoquinoline with elemental sulphur.

5 Claims, No Drawings

PROCESS FOR THE PREPARATION OF 3,4-DIHYDROISOQUINOLINE

FIELD OF INVENTION

The invention relates to a new process for the preparation of 3,4-dihydroisoquinoline.

BACKGROUND OF INVENTION

The isoquinoline derivatives, which are unsubstituted in 1-position, are very important starting materials as well as intermediates in the synthesis of different substituted and condensed isoquinolines. By using the Reissert compounds obtained from the 3,4-dihydroisoquinolines many substituted isoquinolines may be prepared (J. Org. Chem. 35, 3119, 1970). The 3,4-dihydroisoquinolines are suitable also for the preparation of condensed isoquinolines which also are found in nature (Chem. Ber. 98, 557, 1965).

The above mentioned synthesis were, however, performed only with 6,7-dialkoxy derivatives since the 3,4-dihydroisoquinolines, which contain an electron donor substituent in 6-position, may be prepared easily by the Bischler-Napieralsky synthesis. The 3,4-dihydroisoquinoline of the invention may be prepared by the Bischler-Napieralsky synthesis only in a very low yield since the starting material, the N-formyl-2-phenylethylamine does not contain an electron donor substituent in para-position and during the reaction mainly the undesired by-products are formed (Ann. 382, 369, 1911).

Therefore those synthesis routes were mainly studied for the preparation of the 3,4-dihydroisoquinoline which are based on the partially dehydrogenation of the easily available 1,2,3,4-tetrahydoisoquinoline. This reaction cannot be stopped, however, at a degree of partial dehydrogenation while using oxidizing agent and so isoquinoline will be formed (Arch. Pharm. 274, 153, 1936). Therefore this method is suitable only for the preparation of the N-substituted derivatives where, due to partial dehydrogenation, quaternary 3,4-dihydroisoquinolinium salts are formed (J. Am. Chem. Soc. 71, 3408 1949). In the newest literature some oxidation methods are described whereby 3,4-dihydoisoquinoline may be obtained. In these processes special oxidizing agents and catalysts (e.g. ruthenium+tert.-buthylhydroperoxyd) are, however, needed so that the widespread use of this process is restricted (J. Chem. Soc. Chem. Comm. 1985, 615). Also isoquinolines are formed in the dehydrogenation reaction performed in the presence of noble metal catalysts (Chem. Ber. 60, 2602, 1927).

An improved process for the preparation of the compound of the invention is described in our earlier application according to which the 3,4-dihydroisoquinolines were prepared by Bischler-Napieralsky synthesis in the presence of Lewis-acids (published Hungarian patent application Nr. T25,548). Although by this process the 3,4-dihydroisoquinolines substituted in the 1-position could be obtained in very high yield, in the case of 3,4-dihydroisoquinoline unsubstituted in the 1-position the corresponding hexachlorostannate is formed only in a 62% yield, from which the base may be set free with some additional loss.

DESCRIPTION OF THE INVENTION

Our invention, by which the selective dehydrogenation of 1,2,3,4-tetrahydroisoquinoline is realized, eliminates the disadvantages of the known processes and provides a method for the preparation of 3,4-dihydroisoquinoline in large amounts and high purity which is more simple and can be carried out easier than the processes known in the art. It has been found that 1,2,3,4-tetrahydroisoquinoline may be selective dehydrogenated to 3,4-dihydroisoquinoline with elemental sulphur in a solvent at 50° to 150° C. In the reaction the end product is obtained in very high yield, in high purity. As solvents alcohols, aromatic hydrocarbons, ethers, etc. may be used.

According to a preferred embodiment of our invention the reaction is performed in toluene or butanol at the boiling point of the solvent. In the reaction 1-mercapto-1,2,3,4-tetrahydroisoquinoline is formed as an intermediate, which cannot be isolated and by hydrogen sulfide elimination it will be spontaneously transformed to 3,4-dihydroisoquinoline. In the dehydrogenation reaction 1 to 10 moles of sulphur is used per 1 mole of the tetrahydroisoquinoline. In a preferred embodiment of the invention the sulphur is used in excess for the complete reaction and is removed by filtration from the reaction mixture after the reaction has been finished. The partial dehydrogenation may be carried out over 4 to 20 hours depending on the solvent applied and the reaction temperature. After cooling the reaction mixture, filtering the excess of the sulphur and evaporation of the solvent the product is obtained as an oil which may be further purified by distillation in vacuo, if desired. The product may be purified also by salt formation or aqueous acidic extraction. In the reaction the 3,4-dihydroisoquinoline is obtained in a 90 to 95% yield.

SPECIFIC EXAMPLES

The process of the invention is shown by the following non-limiting Examples.

Example 1

30.0 g of 1,2,3,4-tetrahydroisoquinoline and 15.0 g of sulphur powder in 200 ml of toluene are refluxed for 6 hours. After cooling the precipitating sulphur is filtered off, the filtrate is extracted with 200 ml of 5% hydrochloric acid. The aqueous solution is made alkaline with 40% sodium hydroxide to pH=10, then extracted with 250 ml of chloroform. The chloroform extract is dried with sodium sulfate and evaporated in vacuo. As residue 28.5 g of 3,4-dihydroisoquinoline are obtained.

Example 2

30.0 g of 1,2,3,4-tetrahydroisoquinoline and 15.0 g of sulphur powder in 200 ml of toluene are refluxed for 7 hours. After cooling the sulphur is filtered off, the filtrate is evaporated in vacuo. The resulting thick oily residue is distilled in vacuo. 27.5 g of 3,4-dihydroisoquinoline are obtained, b.p. 64°-67° C. at 0.6 mmHg.

Example 3

6.0 g of 1,2,3,4-tetrahydroisoquinoline and 3.0 g of sulphur powder in 40 ml of n-butanol are refluxed for 7 hours. After cooling the sulphur is filtered off, the filtrate is evaporated in vacuo. The residing oily product is converted with saturated alcoholic picric acid to the picrate. 12.0 g of 3,4-dihydroisoquinoline-picrate are obtained, mp. 176°-177° C. Literature mp. 176°-177° C. (J. A. Chem. Soc. 72, 2962, 1950).

Example 4

6.0 g of 1,2,3,4-tetrahydroisoquinoline and 3.0 g of sulphur powder in 40 ml of dioxane are refluxed for 20 hours. The reaction mixture is evaporated, to the residue 60 ml of ether are added, the precipitated sulphur is filtered off and the filtrate is evaporated. 5.7 g of 3,4-dihydroisoquinoline are obtained.

We claim:

1. A process for the preparation of a 3,4-dihydroisoquinoline which comprises dehydrogenating a 1,2,3,4-tetrahydroisoquinoline with elemental sulphur, and recovering the 3,4-dihydroisoquinoline thus obtained.

2. The process defined in claim 1 which comprises performing the dehydrogenation in a solvent medium at 50° to 150° C.

3. The process defined in claim 2 wherein the dehydrogenation is carried out at the boiling point of the solvent medium.

4. The process defined in claim 2 wherein the solvent medium is selected from the group which consists of alcohols, aromatic hydrocarbons and ethers.

5. The process defined in claim 1 comprises using 1 to 10 moles of sulphur per 1 mole of 1,2,3,4-tetrahydroisoquinoline.

* * * * *